Figure 1:
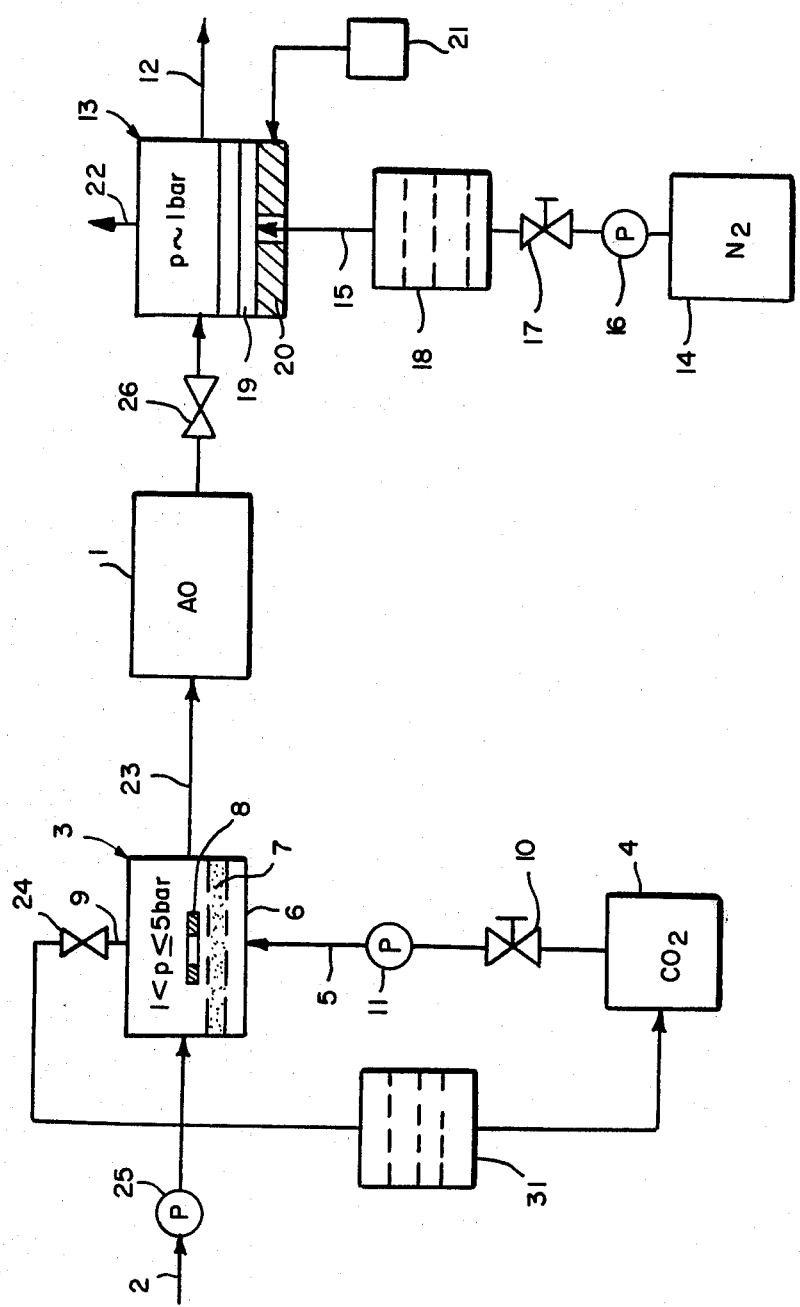

United States Patent [19]

Reis et al.

[11] 4,268,367
[45] May 19, 1981

[54] ELECTROLYTIC PROCESS FOR THE STERILIZATION OF LIQUIDS

[75] Inventors: August K. Reis, Munich; Norbert L. Kirmaier, Aschheim; Helmut Determann, Starnberg; Joachim Thiery, Mannheim; Rolf Haker, Frankenthal; Dietrich Krüger, Schriesheim, all of Fed. Rep. of Germany

[73] Assignee: Institut fur Biomedizinische Technik, Munich, Fed. Rep. of Germany

[21] Appl. No.: 51,625

[22] PCT Filed: May 11, 1979

[86] PCT No.: PCT/DE78/00024

§ 371 Date: May 11, 1979

§ 102(e) Date: May 11, 1979

[87] PCT Pub. No.: WO79/00145

PCT Pub. Date: Mar. 22, 1979

[51] Int. Cl.³ .............................................. C02F 1/46
[52] U.S. Cl. ............................... 204/149; 204/130; 204/277; 204/278
[58] Field of Search ............... 204/130, 149, 151, 152, 204/186; 210/243, 64, 63 R

[56] References Cited

U.S. PATENT DOCUMENTS

| | | | |
|---|---|---|---|
| 3,135,674 | 6/1964 | Ruetschi | 204/151 |
| 3,334,035 | 8/1967 | Dews et al. | 204/149 X |
| 3,440,157 | 4/1969 | Gunther | 204/149 X |
| 3,523,891 | 8/1970 | Mehl | 204/149 X |
| 3,753,886 | 8/1973 | Myers | 204/149 X |
| 4,013,554 | 3/1977 | Reis et al. | 204/149 X |
| 4,098,660 | 7/1978 | Eibl et al. | 204/149 X |
| 4,188,278 | 2/1980 | Reis et al. | 204/149 X |

FOREIGN PATENT DOCUMENTS 150318  8/1919  United Kingdom .

Primary Examiner—Edward S. Williams
Attorney, Agent, or Firm—Donald Brown

[57] ABSTRACT

Liquids with a very low conductivity are sterilized by means of anodic oxidation. For the purpose of increasing the conductivity without using chemically soluble additives, a gas which increases the conductivity, in particular $CO_2$, is fed to the liquid before the anodic oxidation. For the purpose of carrying out the process, a device with an oxidation reactor (1) has a feed line (5), on the inlet side, for the gas to be fed in and a venting means (22) on the outlet side.

5 Claims, 2 Drawing Figures

ELECTROLYTIC PROCESS FOR THE STERILIZATION OF LIQUIDS

The invention relates to a process for the sterilisation of liquids having a very low conductivity by means of anodic oxidation, and a device for carrying out the process.

The invention is intended for application, in particular, in the sterilisation of liquids for use in the pharmaceutical industry and in the medical field.

When distilled water or demineralised water is used in the medical field or in the pharmaceutical industry, this water is passed from a central supply point in a factory or hospital to the particular place of use via an appropriate line. There is the danger here that the water will be re-infected. An additional sterilisation is thus necessary at the actual place of use. This is effected in a known manner, for example by heating, whereupon subsequent cooling is of course necessary. Sterilisation by means of ionising rays is also known. Expensive equipment is of course necessary for sterilisation by means of radiation. Sterilisation by means of a filter has also been attempted, but the problem that complete sterilisation can only be achieved with great difficulty occurred.

A process for sterilisation by means of anodic oxidation and a device for carrying out this process are known, for example from German Offenlegungsschrift No. 2,324,795. So that the anodic oxidation can be carried out, the liquid must have an adequate conductivity, since the power consumption otherwise becomes so high that for economic reasons the process can no longer be used. It is indeed known to add, for example, NaCl to the liquid during the anodic oxidation and thus to increase the conductivity and hence to reduce the energy consumption required. However, the addition of foreign substances is not permitted in the case of certain liquids to be used in the pharmaceutical field or in the medical field.

The object of the invention is to provide a process for sterilising liquids having a very low conductivity by means of anodic oxidation, which can be used, in particular, for the sterilisation of demineralised or distilled water in the pharmaceutical or medical field at the place of use. A device for carrying out this process is also to be provided.

According to a further developement of the invention, the device is intended to be designed so that a regulating device is provided for establishing a given conductivity during the anodic oxidation.

This object is achieved by a process for the sterilisation of liquids having a very low conductivity by means of anodic oxidation, which is characterised, according to the invention, in that a gas which increases the conductivity of the liquid is fed thereto and the anodic oxidation is then carried out. In this manner, anodic oxidation with a low consumption of energy and without the addition of foreign substances which are soluble chemically is possible.

The device for carrying out the process is characterised, according to the invention, by an oxidation reactor with an inlet and an outlet, a feeding means located on the inlet side for feeding in a gas and a venting means provided on the outlet side.

According to a further development of the invention, the process is characterised in that the gas fed in is removed from the liquid after the anodic oxidation.

In a further development of the invention, the gas is removed by means of venting with an inert gas. Particularly rapid and complete removal of the gas fed in is achieved in this manner.

A further development of the invention is characterised in that to increase the proportion of gas to be fed in, the pressure in the liquid to be sterilised by means of anodic oxidation is increased whilst this gas is fed in, until the anodic oxidation has ended. The conductivity is increased still further by the greater absorbability of the gas in the liquid which is thereby achieved.

According to a further development of the invention, the device is characterised in that an area of large flow cross-section is provided on the inlet side of the oxidation reactor and in that the gas can be passed into this area. The interaction between the liquid and the gas introduced and thus the solution thereof in the liquid is increased in this manner.

At the inlet of the feeding means in the area of high flow cross-section, the device has a means of finely distributing the entering gas. Greater solubility of the gas and thus higher conductivity is thereby achieved.

A particular embodiment of the invention is characterised in that a throttle point is provided on the outlet side before the venting means. The liquid in the oxidation reactor is thus under pressure, as a result of which a larger amount of the gas can be dissolved in the liquid.

A further development of the invention is characterised in that the venting means has an area of relatively high flow cross-section with a gas outlet, and a feeding means for passing an inert gas into this area is provided, and this results in the gas dissolved on the inlet side being completely driven out of the liquid.

Figure 2:
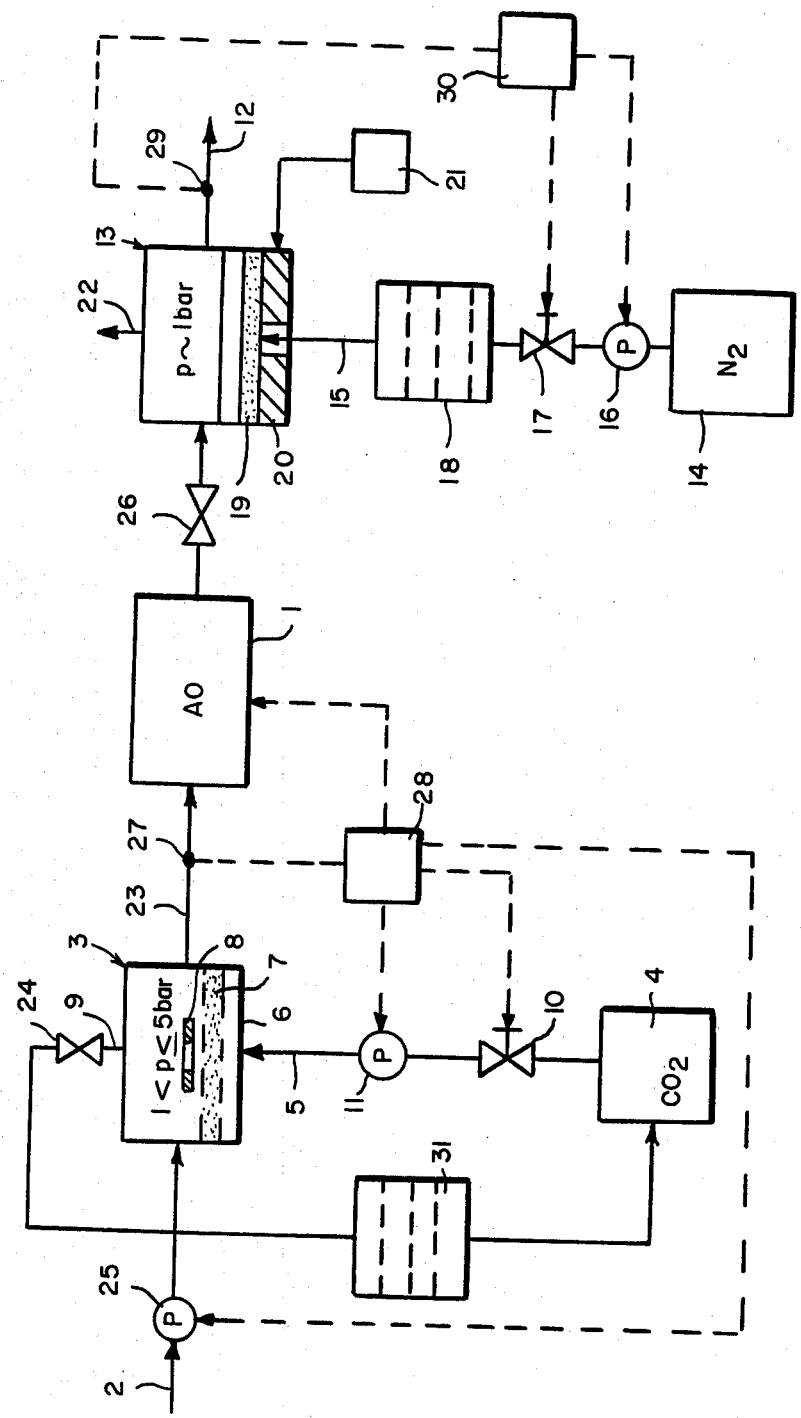

Further characteristics and advantageous features of the invention can be obtained from the description of illustrative embodiments with the aid of the figures. In the figures:

FIG. 1 shows a schematic representation of the device or arrangement according to the invention; and FIG. 2 shows a further development of the invention.

In the figures, the oxidation reactor is designated 1. It can preferably be in the form of a bar grid bundle cell, as is proposed in the pending Patent Application No. P 27 57 854 made by the Applicant Company. The fluid to be sterilised, in particular demineralised water or distilled water, is fed into the oxidation reactor on the inlet side via an inlet line 2. A gas-mixing tank 3 through which the liquid passes is provided upstream of the oxidation reactor. A feed line 5 connected to a $CO_2$ reservoir 4 is provided on the underside of the gas-mixing tank. A porous layer 7 which occupies the entire cross-section of the gas-mixing tank is provided at a distance from the bottom 6 of the gas-mixing tank. A stirrer 8 is located in the gas-mixing tank for stirring the liquid running through. On the upper side, the gas-mixing tank has an opening 9 through which the gas can escape. A throttle valve 10 and a pump 11 by means of which the gas can be passed into the gas-mixing tank from the reservoir 4 under a pre-selected pressure are provided in the feed line 5. Instead of the porous layer, it is also possible to use perforated pipes, tubes or sieve trays, or other means of ensuring fine distribution of the gas in the liquid.

An outlet line 12 via which the sterilised fluid is passed to the user is provided on the outlet side of the oxidation reactor. A gas-demixing tank 13 is provided downstream from the oxidation reactor. A line 15 connected to a $N_2$ reservoir 14 leads into the bottom of the tank. A pump 16 and a throttle valve 17 are provided in the line 15 between the reservoir 14 and the gas-demixing tank 13, for adjusting the pressure of the gas to be fed in via line 15. Furthermore, an inert gas sterilisation filter 18 for sterilising the gas is located upstream of the inlet into the gas-demixing tank.

A porous layer 19 covering the entire cross-section of the tank is provided at a short distance from the bottom of the gas de-mixing tank 13. A vibration device 20, which can be adjusted by means of an electronic control 21, is provided at the bottom of the gas-demixing tank. A venting pipe 22 for discharge of the gas is provided on the upper side of the gas-demixing tank. If desired, it is also possible to provide an opening in the cover of the tank, instead of the pipe. In this case also, instead of the porous layer, it is possible to use other known means of making fine distribution of the gas in the liquid possible.

Using the device described above, the process is carried out by a procedure in which the liquid passed via the inlet line 2 enters the gas-mixing tank. $CO_2$ is fed into the tank from the bottom via feed line 5. On passing through the porous layer 7, the $CO_2$ is distributed finely over the entire cross-section of the tank, so that high interaction and thus very high solution in the water is effected. The solution of the $CO_2$ is intensified further by operating the stirrer 8. Excess undissolved $CO_2$ can leave the tank from the top through opening 9.

The liquid, which now has an adequate conductivity, flows via a connecting line 23 into the oxidation reactor, where actual sterilisation takes place. The liquid leaving the oxidation reactor then passes into the gas-demixing tank. $N_2$ gas is fed into this tank from the bottom, and enters the water in a finely distributed form through the porous layer and drives out all of the dissolved $CO_2$. The size of the gas-demixing tank determines the residence time of the liquid in this tank. The tank is chosen so that the dissolved $CO_2$ is driven out under the given pressure of the $N_2$ gas to be fed in. Conversely, for a given size of tank, the pressure of the $N_2$ is chosen so that the $CO_2$ gas is adequately driven out. The water, which is now completely sterilised and free from all foreign substances, is fed to the place of use via outlet line 12.

The object of the invention is achieved in an optimum manner with an embodiment in which the liquid in the oxidation reactor and in the gas-mixing tank is preferably under a pressure of more than 1 to 5 bars. In this embodiment, which is shown in FIG. 1, the opening 9 is in the form of a pipe, which leads back to the $CO_2$ reservoir 4 via a throttle valve 24 and a gas purification device 31. Furthermore, a pump 25 is provided on the inlet side upstream of the gas-mixing tank 3. A throttle point 26, in which letting down of pressure is effected, is provided on the outlet side of the oxidation reactor 1 upstream of the gas-demixing tank 13.

The device operates in a manner such that a given pressure of water of more than 1 bar and up to about 5 bars is produced with the pump 25. The pressure in feed line 5 is correspondingly adjusted to a higher valve so that adequate solution of the $CO_2$ takes place. $CO_2$ escaping via opening 9 is recycled to the $CO_2$ reservoir. After carrying out the anodic oxidation in the oxidation reactor, the pressure is let down by means of the throttle valve 26, whereupon a considerable proportion of the dissolved $CO_2$ is already released from the solution without further action of external agents. Finally, all the $CO_2$ is driven out of the water by the action of the $N_2$ gas fed in under pressure.

The conductivity which can be seen from Table 1 was produced in the case of distilled water using the process described above. The table shows the conductivity without and with $CO_2$ fed in, the $CO_2$ being fed in to saturation in the latter case. In the last three lines, the values which were measured after the $CO_2$ had been driven out with the aid of $N_2$ over a period of one, two and five minutes are given.

TABLE 1

Introduction of $CO_2$ into distilled water with subsequent blowing out with $N_2$

| Nature or condition of water | Temperature T (°C.) | Conductivity (μs/cm) |
|---|---|---|
| Distilled water, without $CO_2$ (stored in air) | 22 | 4 |
| Distilled water, with $CO_2$ | 21 | 37 |
| 1 minute blowing out with $N_2$ | 20 | 11 |
| 2 minutes blowing out with $N_2$ | 20 | 5 |
| 5 minutes blowing out with $N_2$ | 19.5 | 3 |

| Nature or condition of water | pH value (—) before feeding in $CO_2$ | $CO_2$ concentration (mmols/l) | Redox potential (mV) |
|---|---|---|---|
| Distilled water, without $CO_2$ (stored in air) | 5.3 | 0.3 | 302 |
| Distilled water with $CO_2$ | 4.25 | 10 | 390 |
| 1 minute blowing out with $N_2$ | 4.93 | 0.8 | 378 |
| 2 minutes blowing out with $N_2$ | 6.08 | 0.2 | 328 |
| 5 minutes blowing out with $N_2$ | 6.64 | 0.1 | 308 |

With regard to the saving of energy, experiments gave the following results: by feeding in $CO_2$, the conductivity of the water entering the oxidation reactor was adjusted to 38 μS/cm. To achieve a current density of 2 mA/cm$^2$ in the oxidation reactor, a current of 200 mA was set up. The cell voltage to be applied was then 290 V. Evaluation by calculation showed that at a conductivity, without the addition of $CO_2$, of 2 μS/cm and with the same current density in the oxidation reactor, a voltage of 4,640 V would be necessary, and at a conductivity of 1 μS/cm and with the same current density, 9,280 V would be necessary. The last two values were calculated, since problem-free functioning of the equipment was impossible experimentally when these voltages were applied and a disruptive breakdown took place. In this experiment, the liquid used was distilled water.

When demineralised water was used, a corresponding experiment gave a voltage to be applied of 240 V at a conductivity of 45 μS/cm and with the same current density. In contrast, if no $CO_2$ had been fed in, the conductivity would have been in the range from 1 to 2 μS/cm. At 2 μS/cm, a cell voltage of 5,400 V would have been necessary, and at 1 μS/cm a cell voltage of 10,800 V would have been necessary.

From the first experiment it is found that the power to be employed is 58 W with $CO_2$ and 1,856 W without $CO_2$. Thus, by the addition, according to the invention, of $CO_2$, only 1/32 of the power which would need to be employed without the addition of $CO_2$ is necessary. In the case of the second experiment with demineralised water, a power of 48 W is necessary with the addition of $CO_2$ and a power of 2,160 W is necessary without the addition of this gas. This means that the power to be employed is 45 times greater without the addition of $CO_2$ than with addition of $CO_2$.

In FIG. 2, an embodiment of the invention is described, the basic construction of which corresponds to the device described above and in which the parts which are the same as in FIG. 1 are designated with the same reference figures. In this embodiment, a measuring sensor 27 which measures the $CO_2$ content and passes an output signal to a regulator 28 is located between the gas-mixing tank and the oxidation reactor. The regulator controls, with its output signal, the $CO_2$ feed and the pressure in the gas-mixing tank or oxidation reactor, as a function of the deviation of the measured $CO_2$ content from the desired value. Instead of the $CO_2$ content, it is also possible to measure the conductivity or the pH value with the measuring sensor. The measuring sensor could also record a combination of these values. As soon as the measured value shows that the anode voltage is not sufficient, even when the $CO_2$ feed is re-adjusted and the increase in pressure is re-adjusted, the regulator can re-adjust, via an output signal, the cell voltage being applied to the oxidation reactor 1 or the current. Automatic operation of the apparatus can be achieved in this manner.

In FIG. 2, a measuring sensor 29 which measures the concentration, in the gas-mixing tank, of the gas fed in is provided at the outlet side of the gas-demixing tank 13. The output signal of the measuring sensor is passed to a regulator 30, which regulates, with its output signal, the feed of $N_2$ gas and the pressure thereof such that the content in the gas-mixing tank 3 of the gas fed in is not exceeded on the outlet side of the gas-demixing tank 13.

In the illustrative embodiment described above, $CO_2$ was used to increase the conductivity. In principle, it is also possible to use other gases which increase the conductivity, such as, for example, $F_2$, if the intended use of the water to be produced permits this. However, $CO_2$ is superior to all other gases because it is neither toxic nor explosive and, on the other hand, can easily be driven out again after the anodic oxidation.

In the illustrative embodiment described above, the $CO_2$ was driven out by means of $N_2$ gas. Instead of $N_2$ gas, it is also possible to use noble gases, in particular helium gas.

We claim:

1. Process for the sterilisation of liquids having a very low conductivity by means of anodic oxidation, characterised in that a gas which increases the conductivity of the liquid is fed thereto and the anodic oxidation is then carried out.

2. Process according to claim 1, characterised in that the gas fed in is removed from the liquid after the anodic oxidation.

3. Process according to claim 2, characterised in that the removal is effected by means of venting with an inert gas.

4. Process according to one of claims 1 to 3, characterised in that in order to increase the proportion of dissolved gas, the pressure in the liquid to be sterilised by means of anodic oxidation is increased whilst feeding in this gas, until the anodic oxidation has ended.

5. Process according to claim 1, characterized in that the gas to be fed in is $CO_2$.

* * * * *